(12) United States Patent
Sorvala

(10) Patent No.: US 9,048,529 B2
(45) Date of Patent: Jun. 2, 2015

(54) RESONATOR STRUCTURE IN SMALL-SIZED RADIO DEVICES

(75) Inventor: Juha Sorvala, Kello (FI)

(73) Assignee: POLAR ELECTRO OY, Kempele (FI)

( * ) Notice: Subject to any disclaimer, the term of this patent is extended or adjusted under 35 U.S.C. 154(b) by 264 days.

(21) Appl. No.: 12/934,399

(22) PCT Filed: Apr. 8, 2009

(86) PCT No.: PCT/FI2009/050265
§ 371 (c)(1),
(2), (4) Date: Sep. 24, 2010

(87) PCT Pub. No.: WO2009/125066
PCT Pub. Date: Oct. 15, 2009

(65) Prior Publication Data
US 2011/0012807 A1 Jan. 20, 2011

(30) Foreign Application Priority Data

Apr. 11, 2008 (FI) ................................ 20085304

(51) Int. Cl.
*H01Q 1/48* (2006.01)
*H01Q 9/04* (2006.01)
*H01Q 1/22* (2006.01)
*H01Q 1/27* (2006.01)
(Continued)

(52) U.S. Cl.
CPC ............ *H01Q 9/0485* (2013.01); *H01Q 1/2283* (2013.01); *H01Q 1/273* (2013.01); *H01Q 9/42* (2013.01); *H01Q 19/005* (2013.01)

(58) Field of Classification Search
CPC .......... H01Q 1/36; H01Q 9/0421; H01Q 9/40
USPC .......................................... 343/846, 829, 841
See application file for complete search history.

(56) References Cited

U.S. PATENT DOCUMENTS 5,907,307 A * 5/1999 Bickert et al. ................. 343/702
5,940,036 A * 8/1999 Oliver et al. ............ 343/700 MS
(Continued)

FOREIGN PATENT DOCUMENTS

EP     1249892 A2   10/2002
EP     1439601 A1   7/2004
(Continued)

OTHER PUBLICATIONS

Jimenez J. Pastor, International Search Report for corresponding International Application No. PCT/F12009/050265, pp. 1-3, Aug. 3, 2009.
(Continued)

*Primary Examiner* — Dameon E Levi
*Assistant Examiner* — Collin Dawkins
(74) *Attorney, Agent, or Firm* — Hoffmann & Baron, LLP

(57) ABSTRACT

A resonator structure of an electric apparatus, wherein the resonator structure is configured to interact with a radio frequency signal. The resonator structure includes a dielectric resonator element configured to resonate as a response to the radio frequency signal for transmitting and/or receiving electromagnetic energy wirelessly, and a conductive grounding structure magnetically coupled with the dielectric resonator element and configured to resonate with the dielectric resonator element. The conductive grounding structure includes at least a portion of the casing of the electric apparatus.

12 Claims, 5 Drawing Sheets

(51) Int. Cl.
*H01Q 9/42* (2006.01)
*H01Q 19/00* (2006.01)

(56) References Cited

U.S. PATENT DOCUMENTS

| | | | |
|---|---|---|---|
| 6,603,375 B2 * | 8/2003 | Pance | 333/219.1 |
| 6,903,692 B2 * | 6/2005 | Kivekas et al. | 343/702 |
| 7,271,774 B2 * | 9/2007 | Puuri | 343/718 |
| 7,417,596 B2 | 8/2008 | Zellweger et al. | |
| 2002/0022459 A1 | 2/2002 | Kobayashi | |
| 2002/0158703 A1 * | 10/2002 | Hasegawa | 333/1.1 |
| 2003/0011448 A1 * | 1/2003 | Pance | 333/219.1 |
| 2003/0043075 A1 * | 3/2003 | Bit-Babik et al. | 343/700 MS |
| 2003/0050032 A1 * | 3/2003 | Masaki | 455/272 |
| 2003/0222827 A1 | 12/2003 | Sung | |
| 2005/0235482 A1 * | 10/2005 | Deaett et al. | 29/600 |
| 2005/0253761 A1 | 11/2005 | Tung | |
| 2006/0227058 A1 * | 10/2006 | Zellweger et al. | 343/718 |
| 2006/0232474 A1 * | 10/2006 | Fox | 343/700 MS |
| 2006/0244668 A1 * | 11/2006 | Iellici et al. | 343/729 |
| 2007/0120740 A1 * | 5/2007 | Iellici et al. | 343/700 MS |
| 2007/0257842 A1 * | 11/2007 | Tseng | 343/700 MS |
| 2008/0001829 A1 * | 1/2008 | Rahola et al. | 343/702 |
| 2008/0058615 A1 * | 3/2008 | Clapp et al. | 600/301 |
| 2009/0273535 A1 | 11/2009 | Lee et al. | |

FOREIGN PATENT DOCUMENTS

| | | |
|---|---|---|
| EP | 1489471 A1 | 12/2004 |
| JP | 2008011281 A | 1/2008 |
| WO | WO2006000631 A1 | 1/2006 |
| WO | WO2008037200 A1 | 4/2008 |

OTHER PUBLICATIONS

Finnish Office Action for corresponding Finnish Application No. 20085304, pp. 1-4, Feb. 26, 2009.

* cited by examiner

SENSOR DEVICE

HEART RATE MONITORING RECEIVER

HEART RATE MONITORING TRANSMITTER

GPS RECEIVER

MOTION SENSOR

RESONATOR STRUCTURE

Fig. 10

RESONATOR STRUCTURE IN SMALL-SIZED RADIO DEVICES

CROSS-REFERENCE TO RELATED APPLICATION

This application is a National Phase application of International Application No. PCT/FI20091050265, filed Apr. 8, 2009, which is incorporated herein by reference.

BACKGROUND

1. Field

The invention relates to a resonator structure for transmitting and/or receiving electromagnetic energy in small-sized radio devices.

2. Description of the Related Art

Lately technology has provided us with small-sized radio devices or personal digital assistants (PDA). One example of such is a wrist computer which is a relatively small apparatus used by a person on his/her wrist. The size of the wrist computers creates certain challenges for the design thereof. One such challenge is the miniaturization of an antenna to be mounted on it.

A resonator-type antenna is often used in small-sized radio devices. The antenna-resonator is a device that resonates and radiates energy. In other words it oscillates electromagnetic waves at certain frequencies, called its resonance frequency, with greater amplitude than at other frequencies and the oscillation is based on the dimensions of the resonator that are integral multiples of the wavelength at the oscillating frequencies.

The small size prevents the use of ordinary resonator antennas where the substrate material is the air because of relatively big volume requirement. Compression of this type of antenna causes the bandwidth of the antenna to be small, increases the carrier frequency of the electromagnetic radiation and limits the gain of the antenna-resonator. Consequently, it is common to replace the air as a substrate with a dielectric material. Since air is replaced with the dielectric material, the physical size of the antenna can be decreased in proportion to the dielectric constant of the substrate material of the resonator. This property is also known as the permittivity. In ordinary air isolated antennas this property cannot be utilized. Further, the wave propagation velocity is somewhere between the speed of radio waves in the substrate, and the speed of radio waves in air.

By adjusting the permittivity of dielectric substrate, the physical length of the resonator may be decreased. Regardless of the decrease in the physical length, the electrical length of the resonator may be the same. In general, the electrical length is different from the physical length. However, they are proportional to each other via the dielectric constant. This is because the electrical constant affects the propagation velocity in the substrate, and the electrical length is the physical length multiplied by the ratio of the propagation time of an electromagnetic signal through the substrate to the propagation time of an electromagnetic wave in free space over a distance equal to the physical length. From another point of view, it can be said that since the air as is replaced with the dielectric material, the electrical length of the resonator can be increased while keeping the physical size constant.

One way to increase the effective size of a radiation structure is to include the ground plane as a part of the antenna structure by enabling the so called "ground plane resonance". Generally, this is achieved by forming an electric field between the open end of the antenna resonator and the ground plane. This electric field enables surface current on the ground plane leading to a ground plane resonance. However, the electric field type of coupling is weak and, therefore, the gain of the radiation structure is low.

As the antenna of the wrist computer is generally the first receiving component in the receiving chain, its role is certainly significant. The transmitter may be, e.g., a belt worn by a person around his/her chest and capable of observing the heart beat rate. Thus, it is important to make the gain of the antenna as high as possible. Since the size of the apparatus prohibits the use of a larger single antenna that could increase the gain, other solutions to improve the antenna gain are needed.

SUMMARY

An object of the invention is to provide a resonator structure for transmitting and/or receiving electromagnetic energy in small-sized radio devices.

According to an aspect of the invention, there is provided a resonator structure as specified in claim 1.

According to another aspect of the invention, there is provided a method as specified in claim 11.

According to another aspect of the invention, there is provided a transmitter as specified in claim 15.

According to another aspect of the invention, there is provided a receiver as specified in claim 16.

Embodiments of the invention are defined in the dependent claims.

BRIEF DESCRIPTION OF THE DRAWINGS

In the following, the invention will be described in greater detail with reference to the embodiments and the accompanying drawings, in which

FIG. 10 shows a block diagram of a sensor device.

DETAILED DESCRIPTION

The following embodiments are exemplary. Although the specification may refer to "an", "one", or "some" embodiment(s) in several locations, this does not necessarily mean that each reference is made to the same embodiment(s), or that a particular feature only applies to a single embodiment. Single features of different embodiments may also be combined to provide other embodiments.

Figure 1:
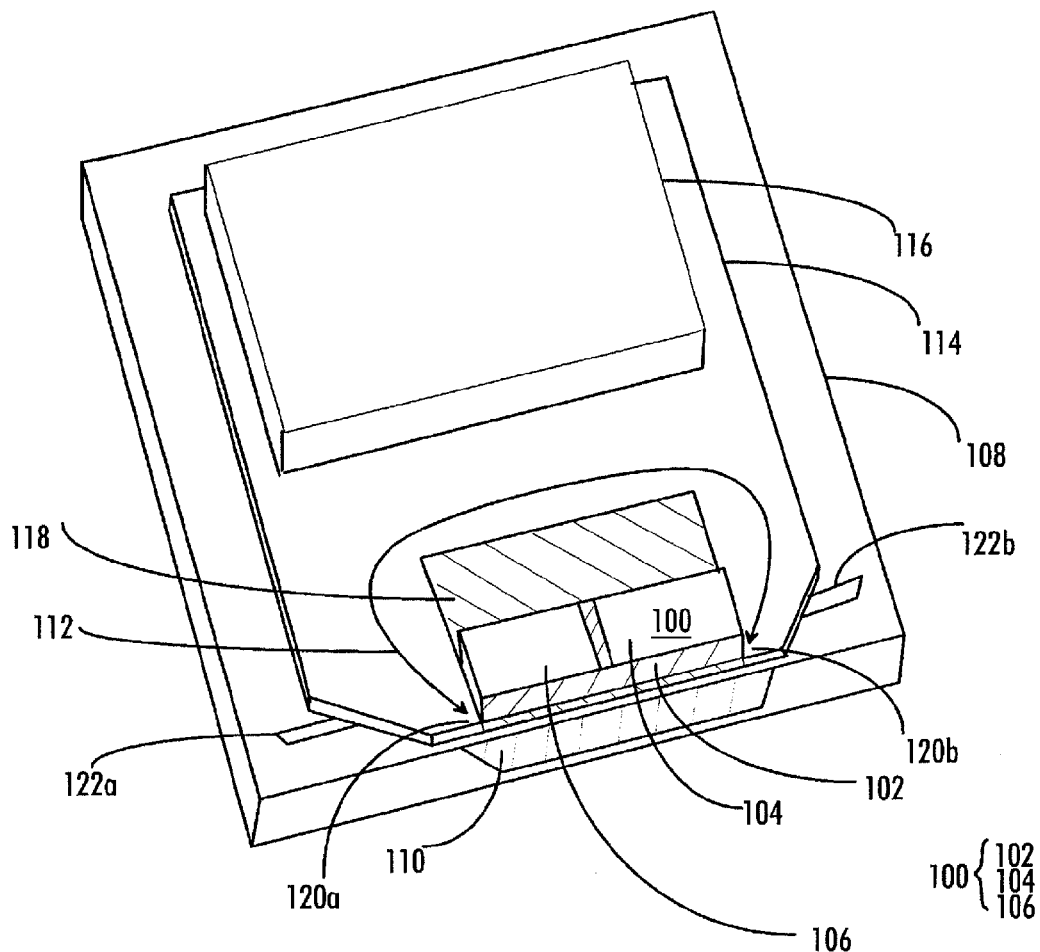
FIG. 1 shows a perspective view of the resonator structure.
Figure 2:
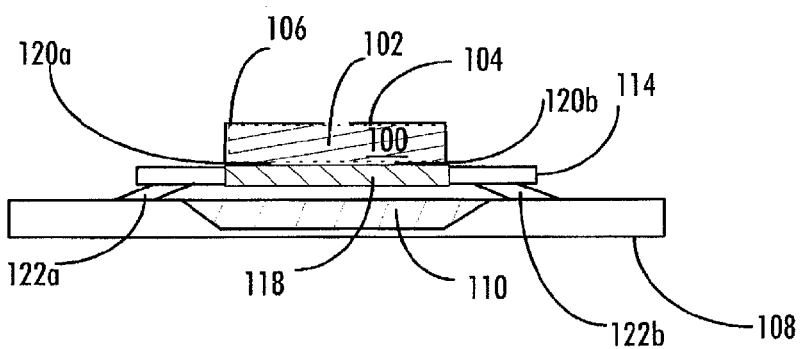
FIG. 2 shows a side view of the resonator structure.

FIG. 1 presents a perspective view of the resonator structure of an electric apparatus, whereas FIG. 2 illustrates a side view of the resonator structure of an electric apparatus. The electric apparatus may be any electrical device such as a wrist computer, a palm computer, a global positioning system (GPS) receiver, a navigator or a sensor unit of a performance monitor, where handling of electromagnetic radio frequencies is desired. The resonator structure may be configured to interact with a radio frequency signal for transmitting and/or receiving electromagnetic energy wirelessly. That is, the resonator structure may be used for transmitting electromagnetic radiation, or it may be used for receiving electromagnetic radiation at a certain radio frequency from another device capable of transmitting electromagnetic radio waves. In an embodiment of the invention, the resonator structure may be used for both transmission and reception. The radio frequency signal may exist in the electromagnetic field surrounding the resonator structure as is the case when the resonator structure is used for receiving, or it may be fed through a wire to the resonator to enable the resonance of the resonator structure in creating radiation for transmission.

In FIGS. 1 and 2 only the logical elements required for understanding the structure of the resonator structure are shown. Other components or elements have been omitted for reasons of simplicity. It is apparent to a person skilled in the art that the radio device configured for transmitting and/or receiving electromagnetic energy may also comprise other functions, components and structures.

Referring to FIGS. 1 and 2, the resonator structure may comprise a dielectric resonator element 100, an electrically conductive grounding structure 108 and an electrically conductive layer 114. The dielectric resonator element 100 may be configured to resonate as a response to the radio frequency signal for transmitting and/or receiving electromagnetic energy wirelessly. It may comprise a dielectric substrate 102 (shown also with diagonal right-leaning solid lines), a feeding radiator element 104 and a parasitic radiation element 106. The specific assembly of the dielectric resonator is illustrated in more detail in FIG. 3 and discussed later.

In general, the dielectric resonator element 100 exhibits resonance for a specific range of radio frequencies. The frequency of the dielectric resonator element 100 is inversely proportional to the wavelength of the electromagnetic wave and the wavelength, on the other hand, is proportional to the electrical length of the resonator. Typically, the dielectric resonator elements 100 in small devices such as wrist computers are relatively small with dimensions less than 1 cm. Consequently the electrical length of the resonator may have to be increased in other manners than by increasing the physical size of the resonator.

One way to do this is to replace the air as a substrate with a material with a high dielectric constant, i.e., dielectric substrate 102. The dielectric constant indicates the extent to which the material concentrates electrostatic lines of flux. In other words, it implies the amount of stored electrical energy in the material relative to the vacuum. In an embodiment, the dielectric constant of the dielectric substrate 102 of a dielectric resonator element 100 is above 30. Due to the high dielectric constant of the substrate material, the radio wave propagation velocity is somewhere between the speed of radio waves in the dielectric substrate 102, and the speed of electromagnetic radio waves in the air. The dielectric constant of the dielectric substrate 102 may be matched with the dimensions of the resonator structure. The electrical length of the resonator structure must be less than one half of the wavelength of the radio frequency electromagnetic field. With small electric apparatuses, such as wrist computers, the dimensions are typically very small. Accordingly in one embodiment, the dielectric constant of the substrate of the dielectric resonator element 100 is selected in such a manner that a quarter of the wavelength of the radio frequency electromagnetic field in the dielectric resonator element 100 is less than one centimeter.

Another way to increase the electrical dimensions of the resonator structure may be to connect the mechanisms or casing of the electric apparatus to the resonator. This can be achieved by enlarging the effective size of the resonator by magnetically coupling at least a portion of the casing of the electric apparatus to the dielectric resonator element 100. The at least a portion of the casing may be electrically grounded and, therefore, called the conductive grounding structure 108. The conductive grounding structure 108 may be further configured to resonate with the dielectric resonator element 100. Since the structure is grounded and it is configured to resonate, the phenomenon may be called a ground plane resonance. The conductive grounding structure 108 may further comprise the at least a portion of the casing, wherein the portion of the casing may be the back cover of the electric apparatus.

As the conductive grounding structure 108 may be comprised by at least a portion of the casing of the electric apparatus and due to the fact that the size limitations for the casing of the electric apparatus are not as strict as they are for the dielectric resonator element 100 inside the electric apparatus, the effective size of the resonator structure may be increased which leads to an enhanced resonator structure performance. The wavelength proportional to the electrical length of the resonator structure may be increased and the resonance frequency may be decreased closer to the desired frequency range.

Generally, regarding resonators, the electromagnetic field flux is significantly larger on the surface of the dielectric resonator element 100 than on the surface of the corresponding resonator with air as a substrate. This is because a resonator with dielectric substrate tends to bind the electromagnetic fields to itself or in the vicinity thereof, called a near field of the resonator/antenna. For this reason, the conductive grounding structure 108 may comprise an empty space 110 below the dielectric resonator element 100 to ensure that the conductive grounding structure 108 would not bind the energy flux placed on the surface of the dielectric resonator element 100 to itself and consequently prevent the radiation from emerging. The empty space 110 may be obtained by removing the metal coating below the dielectric resonator element 100 as shown in FIGS. 1 and 2 with diagonal right-leaning dashed lines and reference number 110.

In an embodiment, the magnetic coupling between the dielectric resonator element 100 and the conductive grounding structure 108 may be achieved by the dielectric resonator element 100, as an exiting component, generating an oscillating (alternating) surface current 112 on the conductive layer 114, on which the dielectric resonator element 100 may be placed. The conductive layer 114 may be, e.g., a printed wiring board including an integrated electrical circuit 116 comprising electrical components such as resistors, capacitors and coils.

In FIG. 1, it is further shown that the surface current 112 may form a current at least partially surrounding a portion of a dielectric material 118. The conductive layer 114 may comprise the portion of the dielectric material 118 shown also with diagonal left-leaning solid lines. Further, a predetermined surface area of the portion of the dielectric material 118 may be used to tune the resonance properties of the resonator structure. The resonance properties of the resonator structure may include, e.g., the resonance frequency of the resonator structure. The resonance frequency increases as the surface area of the portion of the dielectric material 118 decreases because the electrical length of the resonator structure decreases. The opposite happens when the size of the portion of the dielectric material 118 is increased.

The surface current 112 may alternate and generate a strong alternating magnetic field on the edges of the dielectric resonator element 100. These locations on the conductive layer 114 are shown in FIGS. 1 and 2 with references 120a and 120b. The strong alternating magnetic field may enable a strong coupling to the ground plane resonance at the conductive grounding structure 108. This strong coupling may improve the performance of the resonator. This way the conductive grounding structure 108 may be electrically coupled with the conductive layer 114. The conductive grounding structure 108 may be coupled to the high-density surface current area 120a and 120b of the conductive layer 114.

In other words, the dielectric resonator element 100 is configured to generate the surface current 112 on the conductive layer 114, thus providing magnetic coupling between the dielectric resonator element 100 and the conductive grounding structure 108.

An embodiment enables freedom in locating the conductive grounding structure 108 in the electric apparatus. The dielectric resonator element 100 may interact with the conductive layer 114 through an electric mechanism by forming a surface current 114 on the conductive layer 114. The conductive layer 114 and the conductive grounding structure 108 may interact with each other though a magnetic mechanism as explained above. The outcome is that the conductive grounding structure 108 and the dielectric resonator element 100 may interact through magnetic coupling as well.

In order to utilize the ground plane resonance and the reflector effect of the conductive grounding structure 108, the conductive grounding structure 108 is grounded and the surface current 112 from the surface of the conducting layer 114 is lead properly to the conductive grounding structure 108.

Accordingly, in an embodiment, the coupling of the conductive layer 114 and the conductive grounding structure 108 may be obtained by applying at least one coupling member 122a and 122b configured to couple the at least a portion of the conductive layer 114 and the conductive grounding structure 108. In other words, a galvanic coupling between the at least a portion of the conductive layer 114 and the conductive grounding structure 108 may be obtained. The at least one coupling member 122a and 122b may be located in such a way that the conductive grounding structure 108 is coupled to the high-density surface current area 120a and 120b of the conductive layer 114. The at least one coupling member 122a and 122b may be configured to lead the surface current 112 from the conducting layer 114 to the conductive grounding structure 108 in order to enable the ground plane resonance by activating the conductive grounding structure 108 to resonate in parallel with the dielectric resonator element 100. The conductive grounding structure 108 may be open in both ends and, therefore, resonates with a half wavelength of the radio frequency electromagnetic field.

Further, the enlargement of the grounded area obtained by coupling the conductive grounding structure 108 as a part of the grounded area with the at least one coupling member 122a and 122b, may be performed in such a way that the electrical length of the grounded area parallel to the placement of the dielectric resonator structure 108, is increased. This is because the direction of the ground plane resonance in the resonator structure is parallel to the placement of the dielectric resonator element 100. Since, in an embodiment, the dielectric resonator element 100 may be placed crosswise in relation to the casing of the electric apparatus, the electrical length of the grounded area may denote the width of the grounded area. According to an embodiment, the largest dimension of the conductive grounding structure 108, oriented equally to the dielectric resonator element 100, is designed in such a manner that the electrical length is maximized in order to reach a half of the wavelength of the electromagnetic field, still keeping the physical dimension less than four centimeters.

The increment of the physical width of the grounded area may be obtained by placing the at least one coupling member 122a and 122b in such a way that they couple the conductive layer 114 to the edges of the conductive grounded structure 108. Further, the at least one coupling member 122a and 122b may be parallel to the conductive layer 114 without any dramatic curves, twists or bends. The coupling members 122a and 122b, in a case where there are two coupling members, may be located at the conductive layer 114 in such a way that the physical distance between the coupling members is maximized. For example, the coupling members may be connected to the opposite edges of the conductive layer 114.

Moreover, the at least one coupling member 122a and 122b may be integrated into the at least a portion of the casing of the electric apparatus to form the electromagnetic coupling between the at least a portion of the conductive layer 114 and the conductive grounding structure 108. The at least a portion of the casing of the electric apparatus may be the conductive grounding structure 108. The integration of the at least one coupling member 122a and 122b into the at least a portion of the casing of the electric apparatus may be obtained by forming stubs or similar contact areas on the conductive grounding structure 108 in locations that correspond to the high-density surface current areas 120a and 120b of the conductive layer 114.

Figure 3:
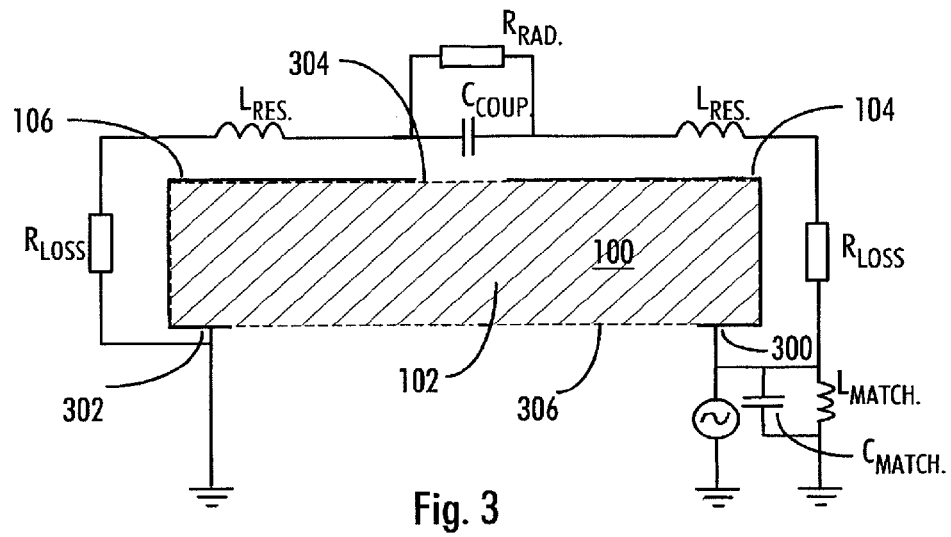
FIG. 3 presents the equivalent circuit of the resonator structure.

Now let us consider the dielectric resonator element 100 in more detail. FIG. 3 illustrates an equivalent circuit of the dielectric resonator element 100. As described earlier, the dielectric resonator element 100 comprises the dielectric substrate 102 (shown also with diagonal right-leaning solid lines), the feeding radiator element 104 and the parasitic radiation element 106. The feeding radiator element 104 may be fed from the feeding point 300 and the parasitic radiation element 106 may be grounded from the other side 302 of the dielectric resonator element 100. There may also exist a narrow gap 304 between the feeding and the parasitic radiation elements 104 and 106, respectively. There exists a capacitive connection between the radiation elements over the narrow gap 304. Further the radiation elements are spaced below the dielectric resonator element 100 by a large gap 306. There may also exist the portion of the dielectric material 118 on the conductive layer 114. This way there may not be any direct galvanic connection between the radiation elements 104 and 106 below the dielectric material, but the only galvanic connection beside the connection on the top of the dielectric resonator element 100 is via the edges of the portion of the dielectric material 118.

Dividing the dielectric resonator element 100 into the feeding radiation element 104 and the parasitic radiation element 106, as shown in FIG. 3, may generate the surface current 112 that generates the ground plane resonance of the resonator structure. The surface current 112 may create a loop in which electromagnetic energy flows through the dielectric resonator element 100 and via the edges of the conductive layer 114, and more particular, via the edges of the portion of the dielectric material 118 back to a feeding point 300 of the dielectric resonator element 100.

The electromagnetic energy may be fed to the dielectric resonator element 100 from the feeding point 300. As the energy flows through the dielectric resonator element 100, it first enters the feeding radiation element 104. From the feeding radiation element 104, the electromagnetic energy drifts through a capacitive coupling to the parasitic radiation element 106 over the narrow gap 304 between the feeding and the parasitic radiation elements 104 and 106, respectively. Since the parasitic radiation element 106 is electrically grounded to the conductive layer 114 from the other end 302, the energy drifts to the conductive layer 114 and further back to the feeding point 300 via the edges of the portion of the dielectric material 118. This high density electric current 112 may generate strong ground plane resonance in the conductive grounding structure 108 via magnetic coupling or via the at least one coupling member as explained earlier.

The narrow gap 304 between the feeding and the parasitic radiation elements and the strong electric field that may be generated over it, together with a ground plane resonance, may form an efficient resonator structure, which may be configured to radiate. Most of the energy fed into the dielectric resonator element 100 may be bound to the dielectric substrate 102 of the dielectric resonator element 100 or to the field in the vicinity thereof. Consequently, the electric field may be strongest at the top of the dielectric resonator element 100 where the narrow gap 304 generates a strong radiation with a symmetric radiation pattern that is directed outwards of the resonator structure 100.

Further, the narrow gap 304 between the feeding and the parasitic radiation elements may offer another way to tune the resonance properties of the resonator structure such as the resonance frequency. By increasing the gap 304, the intensity of the capacitive coupling changes and this affects the resonance frequency of the resonator structure.

The other components in FIG. 3 may be for matching the impedance of the system and for representing losses of the system. Further, the feeding and parasitic radiation elements have their own natural inductances represented by $L_{res}$ in FIG. 3. $R_{rad}$ represents the radiation of the resonator structure.

Figure 8:
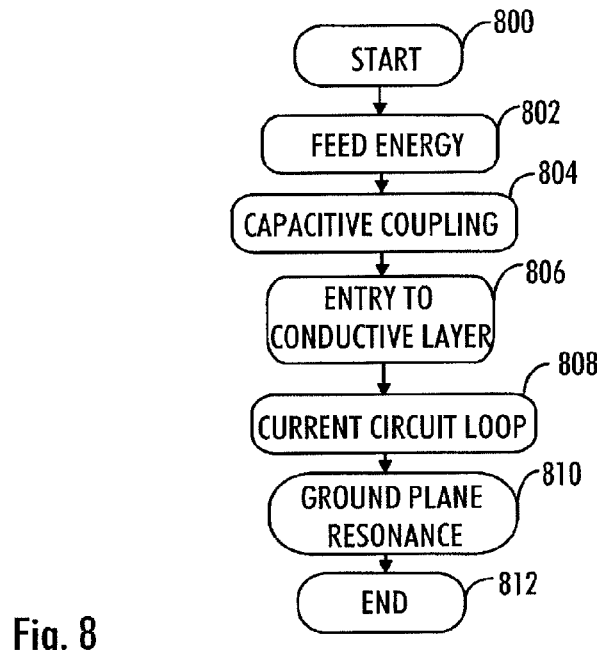
FIG. 8 illustrates the process for generating a ground plane resonance on the conductive grounded structure.

The creation of the ground plane resonance is shown as a flow diagram in FIG. 8. The process starts in 800. In step 802, energy may be fed to the resonator from the feeding point 300. The energy may alternatively be received from the electromagnetic fields in the surrounding environment.

In step 804, the energy may flow across the feeding radiation element 104 and via a capacitive coupling to the parasitic radiation element 106 over the narrow gap 304 between the feeding and the parasitic radiation elements. This way the energy may drift through the dielectric resonator element 100.

In step 806, the energy drifts to the grounded end 302 of the parasitic resonator element 106 and enters the conductive layer 114. In step 808, the surface current 112 may form a loop at least partly surrounding the portion of the dielectric material 118 on the conductive layer 114. The electromagnetic energy flows via the edges of the portion of the dielectric material 118 back to a feeding point 300 of the dielectric resonator element 100. In step 810, the high density electric current 112 may generate strong ground plane resonance in the conductive grounding structure 108 via magnetic coupling or via the at least one coupling member as explained above. The process ends in step 812.

Figure 4:
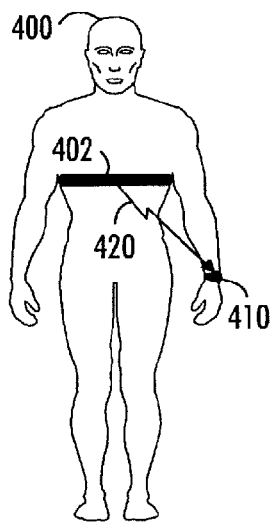
FIG. 4 illustrates an embodiment of an apparatus comprising the resonator structure.

FIG. 4 represents one possible embodiment of the electric apparatus comprising the resonator structure. The resonator structure may be comprised in a wrist device such as, e.g., a heart rate monitoring receiver 410. In FIG. 4, a person 400 wears the heart rate monitoring receiver 410 and a heart rate monitoring transmitter 402 that may be configured to measure a person's heart beat and possibly other metrics such as an electrocardiogram. The receiver 410 of the user-specific heart rate monitoring system may be further configured to transmit information regarding the measurements through an electromagnetic connection 420 between the heart rate monitoring transmitter 402 and the heart rate monitoring receiver 410. The electromagnetic connection 420 may be wireless and it may utilize the Bluetooth® standard, or any other suitable standard/non-standard wireless communication means utilizing electric and/or magnetic fields.

As seen from FIG. 4, the first element in the receiver chain in this case is the antenna of the wrist device comprising the resonator structure of the embodiment. Thus, to obtain a strong gain with the desired frequency range and bandwidth for the resonator structure is certainly an important task.

Figure 5:
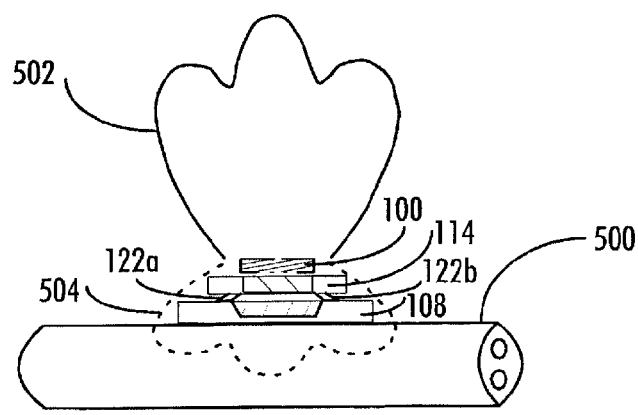
FIG. 5 presents the directional properties of a radiation pattern of the resonator structure.

When analyzing the performance of an antenna, the location in which it will be eventually placed should be taken into consideration. For example, if the location of the resonator structure is in a wrist computer placed on top of a person's wrist 500 as shown in FIG. 5, the absorbing tissues of the wrist 500 should be taken into account. In general, the performance of an antenna decreases when placed in the vicinity of an absorbing tissue.

In FIG. 5, the resonator structure comprising the dielectric resonator element 100, the conductive layer 114 and the conductive grounding structure 108 may generate a first radiation pattern 502 directed in the desired direction opposite to the absorbing tissue of the wrist 500. The conductive grounding structure 108 may comprise a portion of the back cover of the electric apparatus. By incorporating the conductive grounding structure 108 that is wider than the dielectric resonator element 100 or the conductive layer 114 to the resonator structure, most of the second radiation pattern 504 generated by the resonator structure and directed in the undesired direction towards the absorbing tissues of the wrist 500 may be reflected in the opposite, desired, direction by the conductive grounding structure 108. Hence, the absorbing tissues of the person's wrist 500 may not absorb as much of the total radiation of the resonator structure as it would in a case where the back cover of the electric apparatus was made of plastic or another non-reflecting or -conducting material.

As the conductive grounding structure 108 may affect the radiation by reflecting a portion of the radiation towards the desired direction, it may be applied to tuning the total radiation pattern of the apparatus. Radiation herein may denote the transmitted and/or received electromagnetic energy. In other words, the conductive grounding structure 108 is configured to provide directionally sensitive interaction with the transmitted and/or received electromagnetic energy. With the directional effect of the conductive grounding structure 108, a type of a transmission or reception beamforming may be obtained. This may be advantageous in situations where, e.g., it is desired that the receiving beam be directed to the sky. This may occur in situations, where the resonator structure is comprised in a navigator, such as a GPS receiver. Furthermore, in the case of transmission, the directional sensitivity reduces the propagation of the electromagnetic radiation to the human tissue, thus reducing possible health risks.

Figure 6:
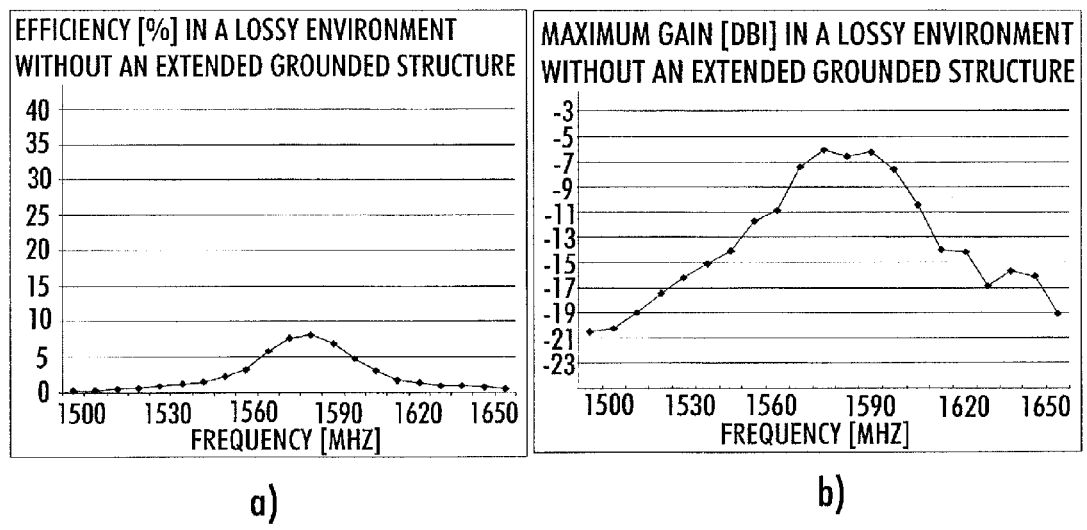
FIG. 6 shows the efficiency and maximum gain of the resonator structure in a lossy environment without an extended area of the grounded structure.
Figure 7:
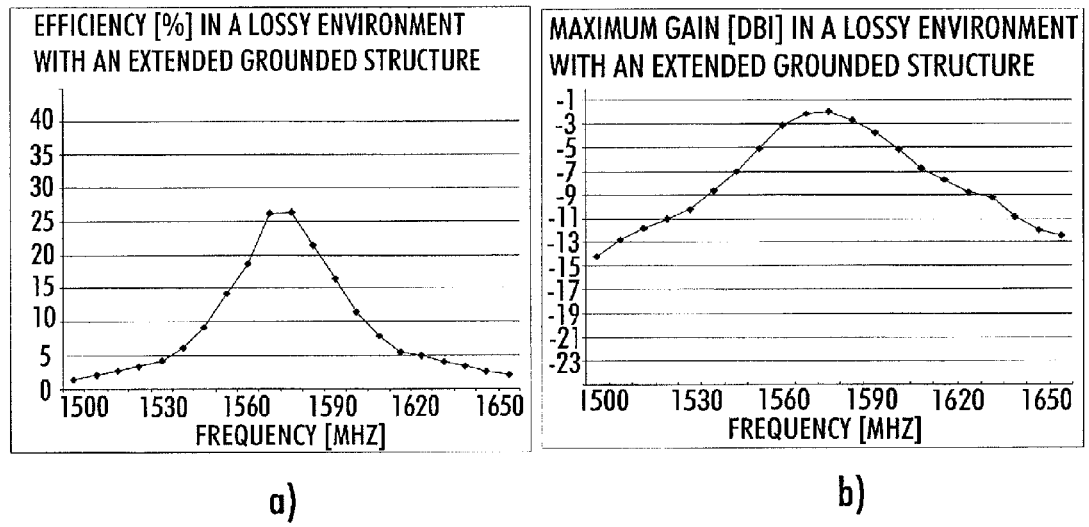
FIG. 7 shows the efficiency and maximum gain of the resonator structure in a lossy environment with the extended area of the grounded structure.

FIGS. 6 and 7 show that the performance of the resonator structure may be improved significantly by incorporating the conductive grounding structure 108 into the resonator structure. FIG. 6a represents the radiation efficiency of the resonator structure in a lossy environment without an extended area of the grounded structure as a function of frequency. The lossy environment may be, for example, in the vicinity of a person's wrist with loading and absorbing tissues. The extended area of the grounded structure may be at least a portion of the back cover of the electric apparatus, comprising the conductive grounding structure 108. In FIG. 6, the conductive grounding structure 108 has not been incorporated as part of the resonator structure. It can be seen that the measured radiation efficiency of the resonator structure without the conductive grounding structure 108 may be only 8%. FIG. 6b shows that the maximum gain of the resonator structure without the conductive grounding structure 108 may be close to −6 dBi. dBi represent the measured gain compared with an isotropic antenna.

FIG. 7 shows similar measures when the back cover of the electric apparatus, comprising the conductive grounding structure 108, has been incorporated as part of the resonator structure. That is, the measures have been conducted with an extended area of the grounded structure. Now it can be seen from the FIG. 7a, that the measured radiation efficiency of the resonator structure with the conductive grounding structure 108 may be increased to 26% from the previous 8%. Similarly, the maximum gain of the resonator structure with the conductive grounding structure 108, shown in FIG. 7b, may be close to −2 dBi instead of −6 dBi.

Figure 9:
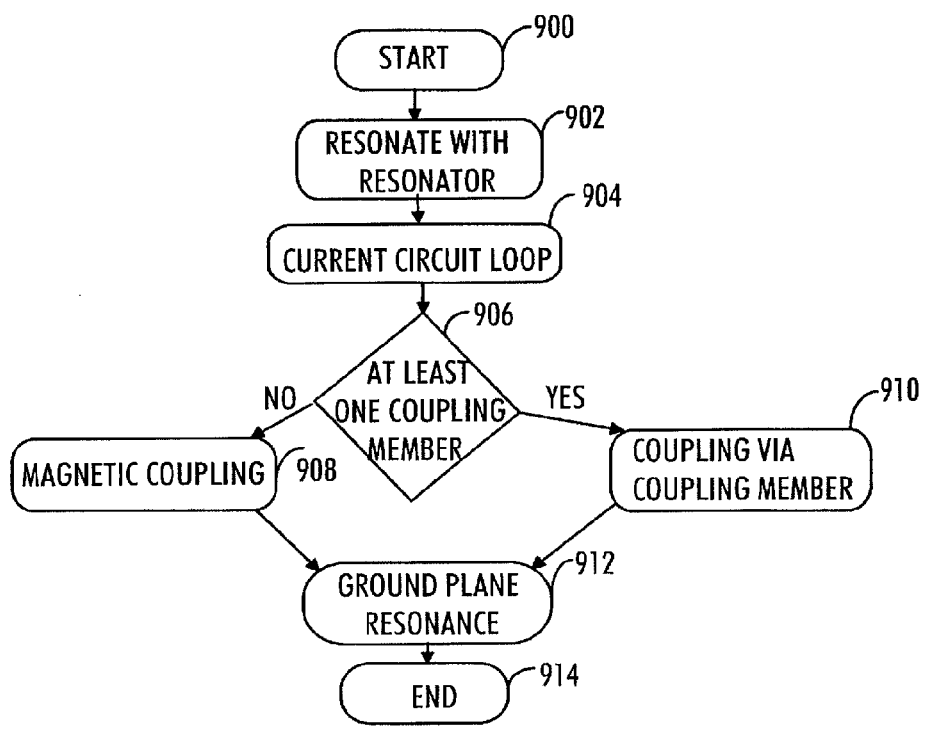
FIG. 9 illustrates the method for generating a resonator structure.

The method for generating the resonator structure is shown in FIG. 9 as flow diagram. The method starts in step 900. In step 902, the dielectric resonator element 100 may resonate as a response to the radio frequency signal for transmitting and/or receiving electromagnetic energy wirelessly. The dielectric resonator element 100 may further create a current circuit loop in step 904 on the conductive layer 114.

In step 906, the method may verify whether there is the at least one coupling member 122a, 122b attached to the conductive layer 114 or not. If there does not exist the at least one coupling member 122a, 122b, the method moves to step 908 in which the coupling between the rest of the resonator structure and the conductive grounding structure 108 is a magnetic coupling. If, on the other hand, there does exist the at least one coupling member 122a, 122b, the method moves to step 910 in which the coupling between the resonator structure and the conductive grounding structure 108 is performed with the at least one coupling member 122a, 122b.

In step 912, the ground plane resonance is generated to the conductive grounding structure 108, wherein the conductive grounding structure 108 resonates in parallel with the dielectric resonator element 100. Further, the conductive grounding structure may provide a directionally sensitive interaction with transmitted and/or received electromagnetic energy. The method ends in step 914.

The resonator structure may be comprised in several electric apparatuses. In an embodiment the resonator structure may be comprised in a navigator device. A person may wear the navigator device on his/her wrist may wear the navigator device. The navigator receiver, such as GPS receiver, on a person's wrist may provide the person with information about his/her speed, distance and other information that can be obtained through satellite positioning.

In an embodiment of the invention, the electric apparatus is a sensor of a performance monitoring system. The sensor includes a heart rate monitoring transmitter, an external GPS receiver or a motion sensor attachable to the user's body. In an embodiment, the electric apparatus is a wrist device, which may be coupled wirelessly to a sensor.

In an embodiment of the invention, the electric apparatus is a receiver and/or transmitter unit connectable to a computer or another external computing device. In such a case, the electric apparatus may be connectable to a USB (Universal Serial Bus) or other standard interface.

Even thought the invention is described in many parts as a transmitting element wherein energy is fed through a wire to the feeding point to make the dielectric resonator element resonate and radiate electromagnetic energy, a person skilled in the art will readily acknowledge that the invention can be applied to a receiver that receives electromagnetic energy from the electromagnetic fields in the surrounding environment. In a case where the resonator element is applied as a receiver, the energy received may be forwarded to the printed wiring board 116 on the conductive layer 114. The printed wiring board may process the received electromagnetic energy and show information to the user via a liquid crystal display or via a similar viewing instrument. The information may contain, e.g., navigation coordinates, speed, heart rate to mention only a few.

Even though the invention is described above with reference to an example according to the accompanying drawings, it is clear that the invention is not restricted thereto but can be modified in several ways within the scope of the appended claims.

Further, for a person skilled in the art, it is clear that the described embodiments may, but are not required to, be combined in various ways with other embodiments to further improve the performance of the resonator structure.

The invention claimed is:

1. A wrist computer, comprising:
a resonator structure that interacts with a radio frequency signal, the resonator structure comprising:
a dielectric resonator element that resonates as a response to the radio frequency signal for at least one of transmitting and receiving electromagnetic energy wirelessly; and
a conductive grounding structure magnetically coupled with the dielectric resonator element and that resonates with the dielectric resonator element, wherein the conductive grounding structure is comprised by at least a portion of the back cover of the casing of the wrist computer, the conductive grounding structure being electrically grounded, the conductive grounding structure having an empty space defined therein, the empty space being disposed below the dielectric resonator element, the empty space being obtained by removing metal coating in the conductive grounding structure below the dielectric resonator;
a conductive layer on which the dielectric resonator element is placed, the conductive grounding structure being magnetically coupled with the conductive layer, the dielectric resonator element generating a surface current on the conductive layer, the surface current providing the magnetic coupling between the dielectric resonator element and the conductive grounding structure; and
a coupling member extending from a position on the conductive layer disposed directly over the empty space to a position on the conductive grounding structure set apart from the empty space.

2. The wrist computer of claim 1, wherein the conductive grounding structure is coupled to a high-density surface current area of the conductive layer.

3. The wrist computer of claim 1, further comprising at least one coupling member that couples the at least a portion of the conductive layer and the conductive grounding structure, wherein the at least one coupling member is a galvanic coupling between the at least a portion of the conductive layer and the conductive grounding structure.

4. The wrist computer of claim 3, wherein the at least one coupling member is integrated into the at least a portion of the back cover of the casing of the wrist computer.

5. The wrist computer of claim 1, wherein the conductive grounding structure provides directionally sensitive interaction with at least one of the transmitted and received electromagnetic energy.

6. The wrist computer of claim 1, wherein the dielectric constant of the dielectric resonator element is selected so that a quarter of the wavelength of a radio frequency electromagnetic field in the dielectric resonator element is less than 1 centimeter.

7. The wrist computer of claim 1, wherein the largest dimension of the conductive grounding structure, oriented equally to the dielectric resonator element, is designed so that the electrical length is maximized in order to reach the half wavelength of the electromagnetic field, still keeping the physical dimension less than four centimeters.

8. The wrist computer of claim 1, wherein the surface current alternates and generates an alternating magnetic field on the edges of the dielectric resonator element.

9. The wrist computer of claim 1, wherein the surface current forms a current that at least partially surrounds a portion of a dielectric material positioned below the dielectric resonator element.

10. A sensor device, comprising:
  at least one of a heart rate monitoring receiver and a heart rate monitoring transmitter that senses heart activity of the user carrying the sensor device;
  an external GPS receiver that determines positioning data of the user carrying the sensor device; and
  a resonator structure that interacts with a radio frequency signal, the resonator structure comprising:
    a dielectric resonator element that resonates as a response to the radio frequency signal for at least one of transmitting and receiving electromagnetic energy wirelessly;
    a conductive grounding structure magnetically coupled with the dielectric resonator element and that resonates with the dielectric resonator element, wherein the conductive grounding structure is comprised by at least a portion of the back cover of the casing of the sensor device the conductive grounding structure being electrically grounded, the conductive grounding structure having an empty space defined therein, the empty space being disposed below the dielectric resonator element, the empty space being obtained by removing metal coating in the conductive grounding structure below the dielectric resonator;
    a conductive layer on which the dielectric resonator element is placed, the conductive grounding structure being magnetically coupled with the conductive layer, the dielectric resonator element generating a surface current on the conductive layer, the surface current providing the magnetic coupling between the dielectric resonator element and the conductive grounding structure; and
    a coupling member extending from a position on the conductive layer disposed directly over the empty space to a position on the conductive grounding structure set apart from the empty space.

11. The sensor device of claim 10, further comprising a motion sensor for determining motion of the user carrying the sensor device.

12. A wrist computer, comprising:
  a resonator structure that interacts with a radio frequency signal, the resonator structure comprising:
  a dielectric resonator element that resonates as a response to the radio frequency signal for at least one of transmitting and receiving electromagnetic energy wirelessly; and
  a conductive grounding structure magnetically coupled with the dielectric resonator element and that resonates with the dielectric resonator element, wherein the conductive grounding structure is comprised by at least a portion of the back cover of the casing of the wrist computer, the conductive grounding structure being electrically grounded; and
  a conductive layer on which the dielectric resonator element is placed, the conductive grounding structure being magnetically coupled with the conductive layer, the dielectric resonator element generating a surface current on the conductive layer, the surface current providing the magnetic coupling between the dielectric resonator element and the conductive grounding structure,
  an empty space being situated between an outer surface of the conductive grounding structure and an outer surface of the dielectric resonator element, the empty space being obtained by removing metal coating in the conductive grounding structure below the dielectric resonator; and
  a coupling member extending from a position on the conductive layer disposed directly over the empty space to a position on the conductive grounding structure set apart from the empty space.

* * * * *